United States Patent [19]
Martin et al.

[11] Patent Number: 5,472,417
[45] Date of Patent: Dec. 5, 1995

[54] TRIPLE LUMEN CATHETER

[75] Inventors: Geoffrey S. Martin; Michael R. LeBlanc, both of Mississauga, Canada

[73] Assignee: Vas-Cath Incorporated, Mississauga, Canada

[21] Appl. No.: 205,331

[22] Filed: Mar. 3, 1994

Related U.S. Application Data

[63] Continuation of Ser. No. 785,351, Oct. 30, 1991, abandoned, which is a continuation of Ser. No. 288,364, Dec. 22, 1988, Pat. No. 5,195,962.

[30] Foreign Application Priority Data

Dec. 22, 1987 [CA] Canada .................................... 555076

[51] Int. Cl.⁶ ..................................................... A61M 3/00
[52] U.S. Cl. ............................ 604/43; 604/264; 604/280
[58] Field of Search ........... 138/111–117; 604/280–284, 604/264, 43, 164–169, 4–7, 101, 102

[56] References Cited

U.S. PATENT DOCUMENTS

| | | | |
|---|---|---|---|
| 3,528,869 | 9/1970 | Derenuik | 156/294 |
| 3,634,924 | 1/1972 | Blake et al. | 29/447 |
| 4,072,146 | 2/1978 | Howes | 604/158 |
| 4,168,703 | 9/1979 | Kenigsberg | 604/280 |
| 4,251,305 | 2/1981 | Becker et al. | 604/103 |
| 4,390,383 | 6/1983 | Van Dongeren | 156/294 |
| 4,406,656 | 4/1983 | Hattler et al. | 604/280 |
| 4,583,968 | 4/1986 | Mahurkar | 604/280 |
| 4,668,221 | 5/1987 | Luther | 604/168 |
| 4,668,225 | 5/1987 | Russo et al. | 604/280 |
| 4,670,009 | 6/1987 | Bullock | 604/280 |
| 4,681,564 | 7/1987 | Landreneau | 604/280 |
| 4,769,005 | 9/1988 | Ginsburg et al. | 604/164 |
| 4,772,268 | 9/1988 | Bates | 604/43 |
| 4,813,429 | 3/1989 | Eshel et al. | 604/43 |
| 4,961,809 | 10/1990 | Martin | 604/280 |
| 4,968,307 | 11/1990 | Dake et al. | 604/280 |
| 5,236,417 | 8/1993 | Wallis | 604/164 |

*Primary Examiner*—C. Fred Rosenbaum
*Assistant Examiner*—Ronald K. Stright, Jr.
*Attorney, Agent, or Firm*—Rogers & Scott

[57] ABSTRACT

The invention provides a triple lumen catheter for use in treatment of humans by inserting the catheter into a blood vessel over a Seldinger guidewire, and using the catheter to extract blood at a selected location in the blood vessel and to return treated blood downstream of the location after treatment. The catheter includes an elongate body and a tip at the distal end of the body. The body has an outer wall and an integral internal septum combining with the outer wall to define a pair of similar C-shaped lumens extending longitudinally in the body. The outer wall of the body defines at least one intake aperture and at least one return aperture and the intake aperture is spaced longitudinally from the tip and from the return aperture with the return aperture being nearer the tip than is the intake lumen. The septum defines a third lumen smaller than the C-shaped lumens and proportioned to slidably receive the guidewire during insertion and to provide a path for the medicament after insertion. The third lumen terminates at the longitudinal extremity of the tip. A connector is attached to the proximal end of the body and a pair of tubes are attached to the connector to carry blood from the intake lumen and to return treated blood to the return lumen. A third smaller tube is attached to the connector and coupled to receive the guidewire during insertion and to provide access for intravenous medicament through the third lumen during use.

1 Claim, 3 Drawing Sheets

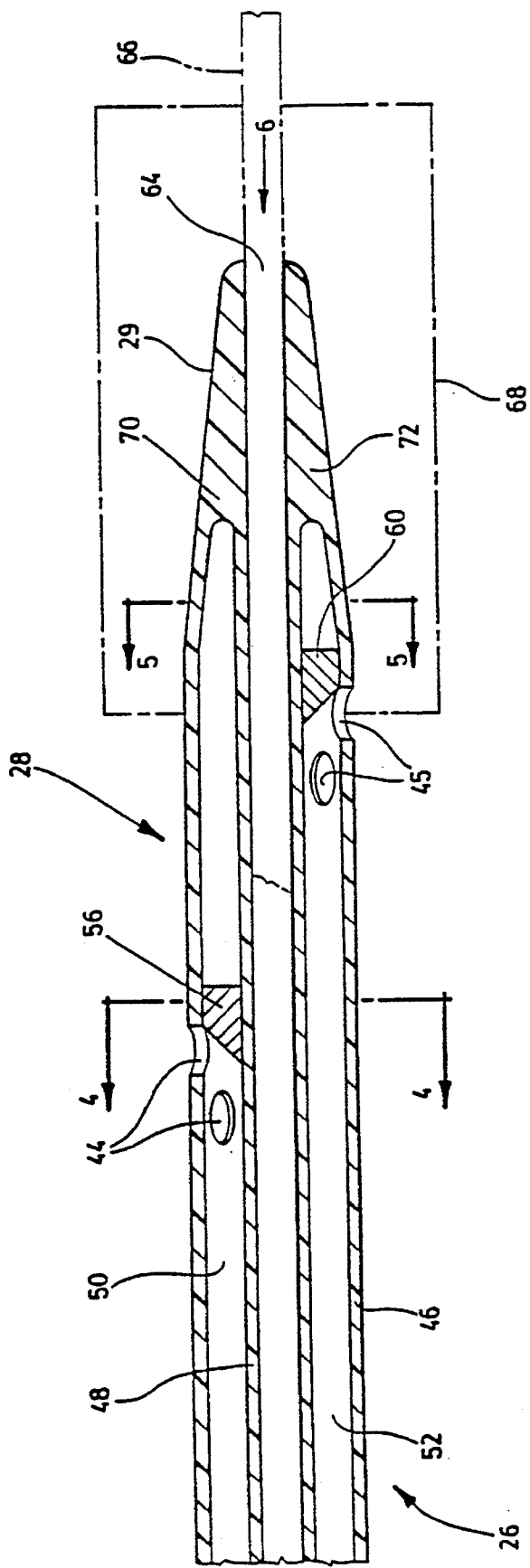
FIG. 3
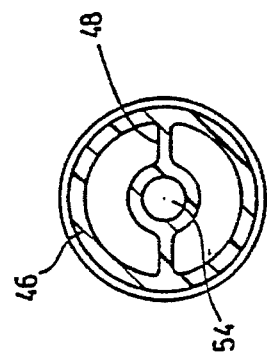
FIG. 6
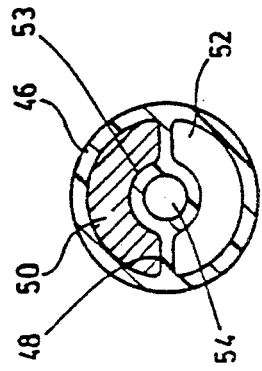
FIG. 5
FIG. 4

TRIPLE LUMEN CATHETER

This application is a continuation of application Ser. No. 07/785,351 filed on Oct. 30, 1991, now abandoned which is a continuation of application Ser. No. 07/288,364 filed on Dec. 22, 1988, and now U.S. Pat. No. 5,195,962.

This invention relates to a multiple lumen catheter and more particularly to such a catheter for insertion into a blood vessel of a patient to be used in haemodialysis treatments. The invention also relates to methods for manufacturing the multiple lumen catheter.

Multiple lumen catheters have been available for many years for a variety of medical purposes. It is only in recent years, however, that such catheters have been developed for use in haemodialysis. The general form of multiple lumen catheters goes back to as early as 1882 when Pfarre patented such a catheter in the United States under Ser. No. 256,590. This patent teaches a flexible dual lumen catheter which is used primarily for cleaning and drainage of, for example, the bladder, rectum, stomach and ear. In this type of catheterization, the catheter is introduced into an existing body orifice without the use of any puncturing needle or guidewire.

More recently, a catheter was developed and patented by Blake et al under U.S. Pat. No. 3,634,924. This 1972 patent teaches a double lumen cardiac balloon catheter which is introduced into a large blood vessel and the balloons inflated to control the flow in the blood vessel. The catheter can in fact be placed by using the balloon as a sail to move with the blood into or through the heart to a position where the catheter takes up its intended function. This patent uses two lumens and teaches a method of making a tip which involves the use of a plug and a wire which retains the shape of one of the lumens during formation of the tip in a moulding technique.

Further patents which teach multiple lumen catheters for general use include the following U.S. Pat. Nos. 701,075; 2,175,726; 2,819,718; 4,072,146; 4,098,275; 4,134,402; 4,406,656 and 4,180,068.

Vascular catheter access by surgical cut-down techniques has been known to the medical profession for many years and, in fact, can be traced back to the 17th century. However, it was only with the introduction of the Seldinger technique in 1953 or thereabouts that a new approach could be used to improve vascular access. This technique was taught in an article published by Seldinger resulting from a presentation made at the Congress of the Northern Association of Medical Radiology at Helsinki in June of 1952. The technique essentially involves the use of a hollow needle to make an initial puncture and then a wire is entered through the needle and positioned in the vessel. The needle is withdrawn and the catheter is entered percutaneously over the wire which is later withdrawn. With this technique it became possible to make less traumatic vascular access and has now become the accepted method of performing access in numerous medical techniques. One of these techniques which has been the subject of much research and development, is haemodialysis.

Haemodialysis can be defined as the temporary removal of blood from a patient for the purpose of extracting or separating toxins therefrom and the return of the cleansed blood to the same patient. Haemodialysis is indicated in patients where renal impairment or failure exists, that is, in cases where the blood is not being properly or sufficiently cleansed, (particularly to remove water) by the kidneys.

In the case of chronic renal impairment or failure, haemodialysis has to be carried out on a repetitive basis. For example, in end stage kidney disease where transplanation of kidneys is not possible or for medical reasons is contraindicated, the patient will have to be dialysed about 100 to 150 times per year. This can result in several thousand accesses to the blood stream to enable the active haemodialysis to be performed over the remaining life of the patient.

Towards the end of 1960, Dr. Stanley Shaldon and colleagues developed, in the Royal Free Hospital in London, England, a technique for haemodialysis by percutaneous catheterization of deep blood vessels, specifically the femoral artery and vein. The technique was described in an article published by Dr. Shaldon and his associates in the Oct. 14th, 1961 edition of The Lancet at Pages 857 to 859. Dr. Shaldon and his associates developed single lumen catheters having tapered tips for entry over a Seldinger wire to be used in haemodialysis. Subsequently, Dr. Shaldon and his colleagues began to insert both inlet and outlet catheters in the femoral vein and this was reported in the British Medical Journal of Jun. 19th, 1963. The purpose of providing both inlet and outlet catheters in the femoral vein was to explore the possibility of a "self-service" approach to dialysis. Dr. Shaldon was subsequently successful in doing this and patients were able to operate reasonably normally while carrying implanted catheters which could be connected to haemodialysis equipment periodically.

Some use was made of a flexible dual lumen catheter inserted by surgical cut-down as early as 1959. An example of such a catheter is that of McIntosh and colleagues which is described in the Journal of the American Medical Association of Feb. 21, 1959 at pages 137 to 138. In this publication, a dual lumen catheter is made of non-toxic vinyl plastic and described as being inserted by cut-down technique into the saphenous vein to the inferior vena cava.

The advantage of dual lumen catheters in haemodialysis is that only one blood vessel access need be affected to establish continued dialysis of the blood, because one lumen serves as the conduit for blood flowing from the patient to the dialysis unit and the other lumen serves as a conduit for blood returning from the dialysis unit to the patient. This contrasts with prior systems where either two insertions were necessary to place the two catheters as was done by Dr. Shaldon, or a single cathether was used with a complicated dialysis machine which alternately removed blood and returned cleansed blood.

The success of Dr. Shaldon in placing catheters which will remain in place for periodic haemodialysis caused further work to be done with different sites. Dr. Shaldon used the femoral vein and in about 1977 Dr. Uldall began clinical testing of a subclavian catheter that would remain in place. An article describing this was published by Dr. Uldall and others in Dialysis and Transplantation, Volume 8, No. 10, in October 1979. Subsequently Dr. Uldall began experimenting with a coaxial dual lumen catheter for subclavian insertion and this resulted in Canadian Patent No. 1,092,927 which issued on Jan. 6, 1981. Although this particular form of catheter has not achieved significant success in the marketplace, it was the forerunner of dual lumen catheters implanted in the subclavian vein for periodic haemodialysis.

The next significant step in the development of a dual lumen catheter for haemodialysis is U.S. Pat. No. 1,150,122 to Martin who produced a catheter which achieved some commercial success. The catheter avoided the disadvantages of the Uldall structure.

A subsequent development is shown in U.S. Pat. No. 4,451,252 also to Martin. This utilizes the well known dual lumen configuration in which the lumens are arranged side-by-side separated by a diametric septum. The structure shown in this patent provides for a tip making it possible to enter a Seldinger wire through one of the lumens and to use this wire as a guide for inserting the catheter percutaneously. Patents to this type of structure followed and include European Patent Application to Edelman published under No. 0 079 719, U.S. Pat. Nos. 4,619,643, 4,583,968, 4,568,329, and U.S. Pat. No. Des. 272,651.

Another approach to creating a tip is to be found in U.S. Pat. No. 4,543,087 to Sommercorn. This patent teaches the use of a separate moulded tip which is inserted into the end of an extrusion to provide the necessary flow paths. However, although the tip has resulted in significant commercial success, it does have the disadvantage that the tip must be inserted into the lumens with resulting discontinuity in the flow path of the return lumen because the blood must meet the end of the insert and pass into an opening through the insert which is of smaller cross-section than the lumen itself.

All of the above examples of haemodialysis catheters which are inserted over a Seldinger wire suffer from the disadvantages that they can not be used readily for intravenous injection of liquid medication. A person who is using haemodialysis therapy with a dual lumen catheter will have to receive a needle for intravenous injection when medication of this kind is required. It would be desirable that the catheter not only perform the function of haemodialysis, but also provide a facility for intravenous injection without further puncturing of the patient's blood vessels. It is one of the objects of the present invention to provide such a catheter.

The foregoing problems associated with haemodialysis catheters may in some instances be specific to that treatment. However, the catheter of the present invention, in overcoming the disadvantages of the prior art of renal dialysis catheters, provides a catheter which has utility in other procedures. Accordingly, although the present description is directed to haemodialysis, such use is exemplary and it will be evident that catheters according to the invention may be used for other procedures.

In one of its aspects the invention provides a triple lumen catheter for use in treatment of humans by inserting the catheter into a blood vessel over a Seldinger guidewire, and using the catheter to extract blood at a selected location in the blood vessel and to return treated blood downstream of the location after treatment. The catheter includes an elongate body and a tip at the distal end of the body. The body has an outer wall and an integral internal septum combining with the outer wall to define a pair of similar C-shaped lumens extending longitudinally in the body. The outer wall of the body defines at least one intake aperture and at least one return aperture and the intake aperture is spaced longitudinally from the tip and from the return aperture with the return aperture being nearer the tip than is the intake lumen. The septum defines a third lumen smaller than the C-shaped lumens and proportioned to slidably receive the guidewire during insertion and to provide a path for the medicament after insertion. The third lumen terminates at the longitudinal extremity of the tip. A connector is attached to the proximal end of the body and a pair of tubes are attached to the connector to carry blood from the intake lumen and to return treated blood to the return lumen. A third smaller tube is attached to the connector and coupled to receive the guidewire during insertion and to provide access for intravenous medicament through the third lumen during use.

This and other aspects of the invention will now be described with reference to the accompanying drawings, in which:

FIG. 3 is an enlarged sectional view of the distal end of the catheter of FIG. 1 drawn on line 3—3 of FIG. 2;

FIGS. 4 and 5 are sectional views taken on the lines 4—4, 5—5, of FIG. 3, respectively, and showing complete sections; and FIG. 6 is an end view of the catheter in the direction generally of arrow 6 of FIG. 3.

The invention will be described in detail with reference to a preferred embodiment to be used for haemodialysis. However the drawings and description are exemplary of the invention and unless otherwise stated, are not intended to be limited by its restraints of size and properties dictated by haemodialysis procedures.

Figure 1:
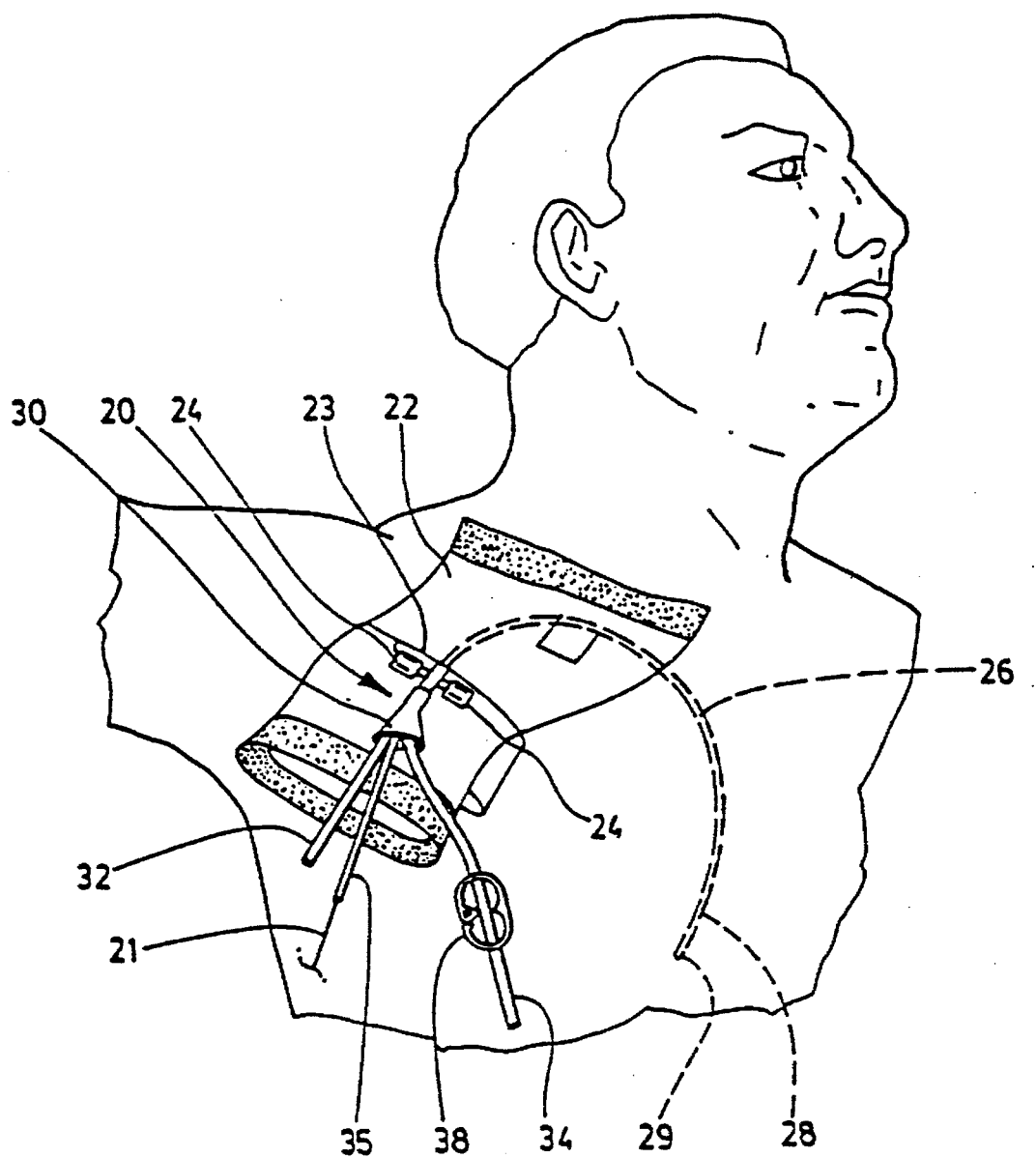
FIG. 1 is a diagrammatic view of a triple lumen catheter according to a preferred embodiment of the present invention, inserted into the subclavian vein of a patient.

Reference is made first to FIG. 1 of the drawings which illustrates a triple lumen catheter, indicated generally by reference numeral 20, according to a preferred embodiment of the present invention, and showing by way of example, a patient receiving the catheter in the subclavian vein using a Seldinger wire 21. The catheter is to be used for haemodialysis treatment and could of course also be entered in a similar fashion in the femoral vein.

The catheter 20 is secured to a conventional dressing 22 by an attachment fitting 23 having wing tabs 24, and the dressing 22, in turn, is secured to the skin of the patient. As shown, the catheter 20 passes through the dressing 22 and, as can be seen in broken outline, an elongate and flexible cylindrical body 26, formed of a polyurethane extrusion, is inserted through the skin and into the subclavian vein in the downstream direction. The catheter 20 has at its distal end 28 a conical tapered tip 29 which is described in greater detail below. The other end of the body 26 is a generally trident-shaped branching connector 30, which protrudes outwardly from and is secured by dressing 22. Cylindrical blood extraction and return tubes 32, 34 and an intravenous (IV) tube 35 are attached to the trident-shaped branching connector 30, a full description of which is provided below. For the moment it is sufficient to state that these tubes are connected to lumens running through the body 26.

Figure 2:
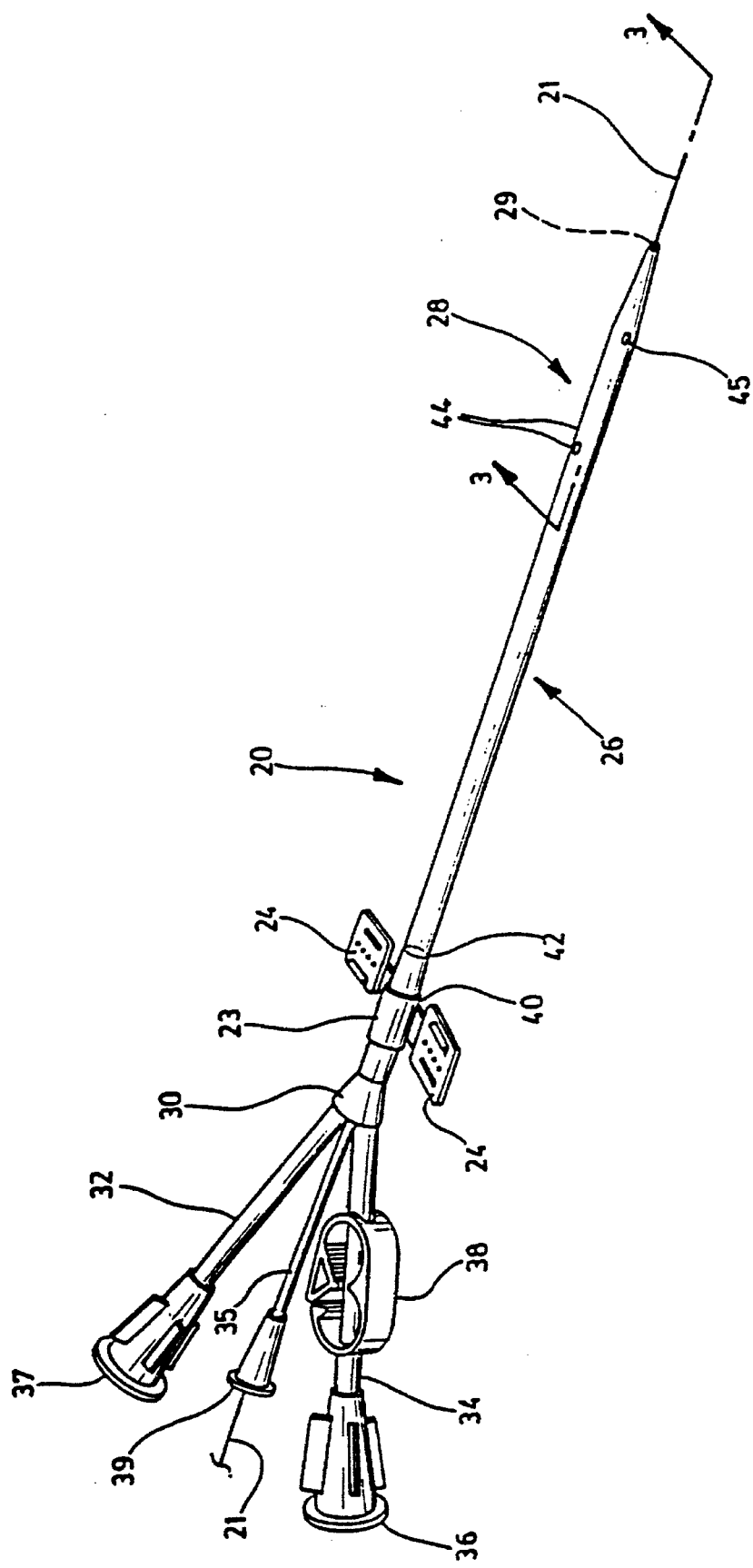
FIG. 2 is a diagrammatic perspective view of the catheter drawn to a larger scale than that used in FIG. 1.

FIG. 2 shows the catheter 20 in greater detail. The body 26 has at its proximal end the connector 30 for receiving the blood extraction and return tubes 32, 34. These tubes terminate at their outer ends in respective female luer fittings 36, 37 for connection to complementary male luer fittings (not shown) leading to a dialysis machine, and carry closure clamps 38 (one of which is shown) to selectively close the tubes.

The IV tube 35 terminates at its outer end in a luer lock fitting 39 for receiving a syringe or male luer lock connector.

The wing tabs 24, sometimes known as suture wings, are formed integrally with a central tubular portion 40 which can rotate on the body 26 and is retained in place by a shoulder on the end of the connector 30 and a second shoulder in a reinforcing portion 42 so that the catheter 20 can be rotated relative to the tabs 24. This rotation is sometimes necessary after insertion of the catheter 20 to re-orientate intake side apertures in the distal end 28 if the apertures happen to be occluded by engagement with the wall of the blood vessel. Details of the apertures are provided below.

As will be described, the reinforcing portion 42 is blended into the body 26 over the length of the portion and assists in strengthening the catheter to minimize the likelihood of kinking. Also, the portion 42 assists in sealing the puncture site where the catheter enters the patient.

As will be described in more detail with reference to subsequent views, the tube 35 is aligned with a central lumen to permit the Seldinger wire 21 to pass through the catheter. The wire exits at tip 29 which is essentially conical so that the catheter can slide over the wire and into the patient during insertion. The extraction and return tubes 32, 34 are linked at connector 30 with lumens in the body 26 to connect with respective groups of side apertures 44, 45 (some of which can be seen in this view) near the distal end of the catheter 28. As a result, when inserted and in use, blood can be removed and returned in a closed loop with a haemodialysis machine using the tubes 32, 34. Between treatments the tube 35 is available for intravenous infusion of liquid medicaments.

Reference is next made to FIGS. 3 to 6 of the drawings which illustrate the distal end 28 including tip 29. The body 26 comprises an outer wall 46 and an integral septum 48 extending diametrically across the body 26 and defining an extraction lumen 50 and a return lumen 52, both lumens being generally C-shaped in cross-section and extending from the proximal end towards the distal end. As best seen in FIG. 4, a bulbous middle portion 53 of the septum 48 projects into the lumens 50, 52 and contains the intravenous (IV) lumen 54 which extends along the longitudinal axis of the body portion 26 from the proximal end to the distal end. This lumen is an extension of the IV tube 35 and is proportioned in this embodiment to receive a 0.038 inch diameter Seldinger wire.

The extraction lumen 50 is blocked short of the tip 29 by a first insert 56 which is formed of polyurethane and bonded in place using a suitable solvent such as cyclohexanone. Extraction apertures 44 are provided in the outer wall 46 of the cylindrical portion 26, just short of the insert 56, to permit blood to flow from the patient's blood vessel into the extraction lumen 50 and thus through the connector 30 to the extraction tube 32 and the dialysis machine. It should be noted that the apertures 44 are conveniently circular but may be of any suitable shape or size including scaphoid. Also, further extraction apertures may be provided around the lumen 50 as required consistent with the aperture nearest the tip being immediately adjacent the insert 56 to minimize dead spaces.

The return lumen 52 is similarly blocked by a second insert 60 immediately adjacent the last of several return apertures 45. This last aperture is positioned closer to the tip 29 than is the last of the intake apertures 44 in the extraction lumen 50 to minimize the risk of cross flow as returning blood finds its way back into the lumen 50. Although some cross-flow is not critical, excess cross-flow will extend the time needed for haemodialysis.

As can be seen in FIGS. 3 and 6, the tip 29 is smoothly rounded at the end 28 of the catheter and tapered gently to facilitate insertion of the catheter 20 into a patient. As mentioned previously, the catheter is intended to be used with a Seldinger wire. In this embodiment the tapered tip 29 is concentric with the axis of the body 26 and with the lumen 54. Accordingly, the centrally located IV lumen 54 extends to the tip 29 and terminates at a circular aperture 64.

The catheter 20 is made from a length of cylindrical polyurethane extrusion forming the cylindrical body 26. The extrusion is cut to the required length and the ends formed by further operations. The formation of the tapered tip 29 will be described with reference firstly to FIG. 3.

Before shaping the tapered tip 29, the inserts 56, 60 are positioned and affixed in the respective lumens 50, 52, as shown in FIG. 3. The inserts are shaped to the cross-section of the lumens and affixed as previously described. A cylindrical wire 66 (shown in chain dotted outline), of corresponding diameter to that of the guide wire 21 (FIG. 2), is inserted through the IV lumen 54 to extend from the distal end of the tubing which is then located in a conical tapered mould 68 (shown in chain-dotted outline in FIG. 3). The extrusion is heated by R.F. and as it softens it is pushed into the mould such that the outer wall 46 and the septum 48 merge at the tip 29. The end of the body assumes a conical tapered shape with a radiused end and the material masses in the lumens 50, 52 forming ends 70, 72. The IV lumen 54 retains its internal shape because it is supported on the wire 66. The now tapered tip is cooled to some extent and then removed from the mould 68 and allowed to cool further and harden.

The deformation of the tip results in a thickening of the outer wall 46 and septum 48 to provide a concentration of material substantially exceeding the concentration of material in the main catheter body, and this facilitates insertion of the catheter.

Because the wire 66 is not deflected at any time from its normal straight condition during the moulding operation, there is no energy stored in the wire and consequently there is no tendency for the wire to deflect the tip from the desired orientation after removal from the mould 68.

The wire can therefore be left inside the tip during cooling. The apertures 44, 45 are then cut or otherwise formed in the outer wall 46 of the body 26. Also, because the extrusion is symmetrical about the wire, the deformed material at the tip will move evenly to both sides of the central septum. The resulting similar masses at ends 70, 72 of the lumens will cool and shrink equally so that the tip will remain concentric about the central or IV lumen 54. This will result in a well formed tapered tip.

In use, as mentioned above, the catheter 20 is inserted such that it points downstream in the patient's blood vessel, that is, the extraction aperture 44 are upstream of the return apertures 45, which, in turn, are upstream of the IV tip aperture 64. When a treatment is in progress the extraction tubes 32, 34 are connected to a dialysis machine which draws blood through the extraction lumen 50 and returns it through return lumen 52 in a similar manner to a conventional dual lumen cannula. Between blood treatments the lumens may be filled with a heparin solution to prevent them from being filled with clotted blood. However, if the patient requires medication or is required to give blood between treatments, the IV lumen 54 may be used. This avoids the trauma and discomfort of the inserting a further needle or catheter into the patient and does not disturb the heparin lock.

Between uses the third lumen may be filled with a relatively small volume of heparin or may be occupied by cylindrical solid and flexible patency obturator, similar to guide wire 21. This obturator prevents the entrance of blood into the lumen and thus eliminates the need for heparin in the third lumen. Generally, it will be easier to keep the third lumen free of blood due to its smaller cross-section, regular shape and absence of side holes.

In addition to this advantage the centrally located lumen offers considerable advantages for insertion and removal of the catheter. As there are no sideholes in the lumen, "J" ended guide wires may be used without the possibility that the guidewire will exit through a sidehole, rather than the end aperture. In addition, because it is easier to keep the smaller lumen free of clotted blood, it should be possible to use a guidewire to replace a catheter which has clotted blood in the blood lumens without dislodging any blood clots which may have accumulated in the blood lumens. This would be done by first entering the Seldinger wire into the third lumen of the catheter in place in the blood vessel, withdrawing this catheter over the wire leaving the wire in place, and then using the wire to guide a replacement catheter over the guide wire.

The exemplary catheter described with reference to the drawings does not have the proportions of a haemodialysis catheter. As mentioned previously, the description is exemplary and in practice, if the catheter is to be used in the subclavian vein it will have proportions as follows. The central lumen will have a diameter of about 0.04 inches to receive a Seldinger wire of diameter 0.038 inches or 0.036 inches. The walls about the central lumen and forming the septum will be about 0.010 inches in thickness and will blend into the outer wall which is about 0.013 inches in thickness. The outer diameter of the body 26 will be 0.149 inches and this will give an area available for blood flow in the lumens of about 0.0048 square inches. The flow rate will be approximately 237 milliliters per minute using accepted pressures to drive the blood through the lumens.

Clearly catheters can be made with a variety of proportions depending upon the use and structures defined by the claims and incorporating the description are within the scope of the invention.

It will be appreciated that various other modifications may be made to the catheter, and to the processes for making parts of the catheter as described, without departing from the scope of the invention, for example, the material used to form the tube and inserts may be any suitable medical grade thermoplastic. Also, the positioning of the apertures and the number of apertures is to some extent a matter of choice. Also, the length of the conical tip can be varied to include apertures in the wall of the tip. While such a structure is more complicated to make, the flow pattern would be advantageous.

Although the catheter has been described in use in haemodyalsis in a subclavian vein it would also be appreciated that it can be used in both femoral and jugular veins, and can also be used in other blood treatments including apheresis, haemoperfusion and non-blood related treatments involving nutrition and drug therapies.

We claim:

1. A triple lumen catheter for use in treatment of humans by inserting the catheter into a blood vessel over a Seldinger guide wire having a round cross-section, and using the catheter to extract blood at a selected location in the blood vessel and to return treated blood downstream of the location after treatment, the catheter comprising:

an elongate body extending about a longitudinal axis from a proximal end to a distal end;

a tip at the distal end of the body;

the body having an outer wall and an integral internal septum combining with the outer wall to define a pair of similar C-shaped lumens extending longitudinally;

the outer wall of the body defining at least one intake aperture and at least one return aperture, the intake aperture being spaced longitudinally from the tip and from the return aperture, and the return aperture being nearer the tip than is the intake aperture sufficient to limit the likelihood that treated blood leaving the return aperture will be inspired into the intake aperture;

one of the C-shaped lumens terminating at the intake aperture to form an intake lumen, and the other of the C-shaped lumens terminating at the return aperture to form a return lumen;

the septum defining a third lumen smaller than the C-shaped lumens and having a round cross-section proportioned to slidably receive the guide wire during insertion and to provide a path for medicament after insertion, the third lumen terminating at the longitudinal extremity of the tip so that the third lumen is as long as the catheter;

a connector attached to said proximal end of the body;

a pair of tubes attached to the connector and coupled by the connector to the respective C-shaped lumens to carry blood from the intake lumen and to return treated blood to the return lumen;

a third smaller tube attached to the connector and coupled by the connector to the third lumen to receive the guide wire during insertion and to provide access for intravenous medicament through the third lumen during use; and the body and the tip combining to present a smooth transition from the cross-section of the body to a smaller cross-section at the distal end.

* * * * *